US00PP29606P3

(12) United States Plant Patent
Stapleton et al.

(10) Patent No.: US PP29,606 P3
(45) Date of Patent: Aug. 21, 2018

(54) COAST REDWOOD TREE WITH PERICLINAL CHIMERIC ALBINISM NAMED 'GRAND MOSAIC'

(50) Latin Name: *Sequoia sempervirens*
Varietal Denomination: Grand Mosaic

(71) Applicant: Thomas Santos Stapleton, Volcano, CA (US)

(72) Inventors: Thomas Santos Stapleton, Volcano, CA (US); Dale Frederick Holderman, Santa Cruz, CA (US)

(73) Assignee: Thomas Santos Stapleton, Volcano, CA (US)

( * ) Notice: Subject to any disclaimer, the term of this patent is extended or adjusted under 35 U.S.C. 154(b) by 0 days.

(21) Appl. No.: 15/530,136

(22) Filed: Dec. 6, 2016

(65) Prior Publication Data

US 2018/0160593 P1 Jun. 7, 2018

(51) Int. Cl.
*A01H 5/00* (2018.01)
*A01H 7/00* (2006.01)

(52) U.S. Cl.
USPC ..... Plt./213
CPC ..... *A01H 7/00* (2013.01)

(58) Field of Classification Search
USPC ..... Plt./213
See application file for complete search history.

(56) References Cited

PUBLICATIONS

Davis, Douglas F. & Holderman, Dale F., The White Redwoods: Ghosts of the Forest, Naturegraph Publishers, Happy Camp, California, United States, Jan. 1, 1980, pp. 33-37. pp. 6.

Fink, Siegfried, Some cases of delayed or induced development of axillary buds from persisting detached meristems in conifers, (journal), Jan. 1984, pp. 44-51, vol. 71(1), American Journal of Botany. pp. 9.

Lineberger, R., "Origin, Development, and Propagation of Chimeras", Texas A&M University. Retrieved from http://aggie-horticulture.tamu.edu/tisscult/chimeras/chimeralec/chimeras.html on Jan. 20, 2014. pp. 4.

Moore, Zane, Coast redwood albinism and mosaicism, (online published article), Dated Mar. 2013, Retrieved from http://www.mdvaden.com/documents/albino_redwoods_chimera.pdf on Aug. 26, 2014. pp. 10.

Sessions, Allen & Yanofsky, Martin F., Dorsoventral patterning in plants, (journal), 1999, pp. 1051-1054, vol. 13, Genes & Development. pp. 5.

Stapleton, Thomas, A perspective on albino redwoods, (online published article), No date, Retrieved from http://www.savetheredwoods.org/blog/a-perspective-on-albino-redwoods/ on Aug. 26, 2014. pp. 3.

Staveley, Brian E., Molecular & developmental biology (BIOL3530): Plant development, No date, pp. 1-5, Retrieved from http://www.mun.ca/biology/desmid/brian/BIOL3530/DB_06/DBNPlant.html on Aug. 27, 2014. pp. 5.

Sterling, Clarence, Growth and vascular development in the shoot apex of *Sequoia sempervirens* (lamb.) endl. I. structure and growth of the shoot apex, (journal), Mar. 1945, pp. 118-126, vol. 32(3), American Journal of Botany. pp. 10.

*Primary Examiner* — Susan McCormick Ewoldt

(57) ABSTRACT

'Grand Mosaic' is a new and distinct variety of albino coast redwood tree characterized by a non-grafted periclinal chimera exhibiting stable albino growth from inside the apical meristem dome. The new variety contains latent axillary and/or accessory buds forming within the internode of primary branches exhibiting phenotypic color expressions ranging from green, albino, chimera or non-chimeric variegation. Latent axillary and/or accessory buds frequently form in the branch collar zone of primary branches and can produce color expressions ranging from green, albino, chimera or non-chimeric variegation. Further, the branches demonstrate horizontal to drooping-like habit and moderate-to-fast growth depending on the amount of albinism compared to other common green redwoods.

11 Drawing Sheets

Figure 1:
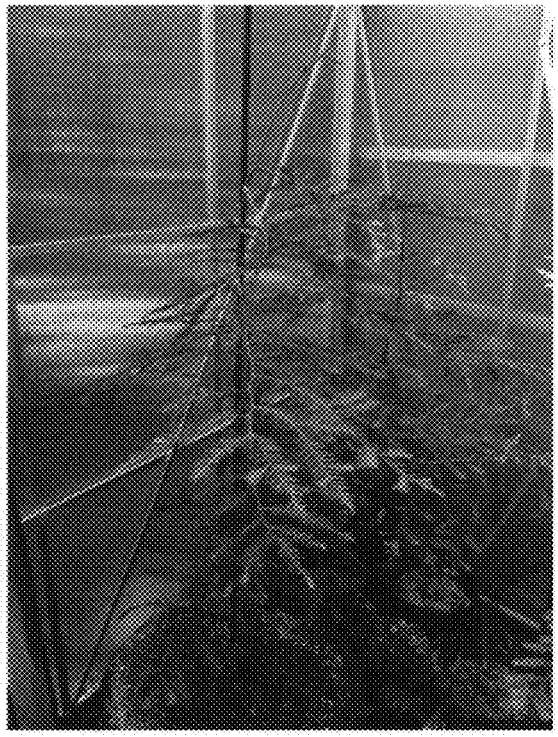

Latin name of the genus and species of the tree claimed: The Coast Redwood tree variety of this invention is botanically identified as *Sequoia sempervirens*.

Variety denomination: The variety denomination is 'Grand Mosaic'.

BACKGROUND OF THE INVENTION

The present invention relates to a new and distinct tree variety of *Sequoia sempervirens*, more commonly known as Coast Redwood tree, having naturally-occurring chimeric characteristics resulting in albinism vegetation.

Specifically, 'Grand Mosaic' is a periclinal chimera exhibiting stable albino growth inside the apical meristem dome. The albinism emerges more prominently beginning in the second year of growth. Tests conducted by the first-named inventor reveal that the present invention has a survival tolerance with up to 65 percent albinism. The buds of the present invention contain several forms of naturally-occurring chimera, including: periclinal, mericlinal, and sectorial. The branches demonstrate color variation, including: green, albino, and chimeric, and non-chimeric variegation; and exhibit a horizontal-to-moderate drooping growth habit. The needles are dense, broad, and singularly arranged with a slightly concave tip pattern. Additionally, under the right conditions, the present invention yields moderate propagation levels via stem and leaf cuttings.

The new variety originated as a result of an ongoing breeding program in Santa Cruz, Calif. The seedling of the present invention was grown from a controlled cross conducted in 1976 where an unnamed, unpatented albino *Sequoia sempervirens* providing the male pollen and the conelets of an unnamed, unpatented green *Sequoia sempervirens* were pollinated. After repeated experimental propagation efforts, asexually-reproduced leaf and stem cuttings took root in a greenhouse laboratory setting in Volcano, Calif. between the years of 2012-2015. These cuttings yielded the stable periclinal chimeric albinism growth characteristic of the present invention.

Coast redwood trees (herein referred to as "redwood") are well known in the industry for their disease and insect resistance, fast growth habit, fire tolerance, and for supporting wildlife habitat. Redwoods are also noted for their height and longevity. These characteristics have led to an increase of the use of this plant as an ornamental feature in landscaped gardens and re-forestation projects. Congruent with similar Coast Redwoods, the present invention is anticipated to reach a height of 18 to 36 meters, maintain tree form, and have a lifespan capacity of 200 to 1000 years.

Albinism in redwoods is a genetic mutation presenting as chlorophyll deficit in the plant's needles and stems. As chlorophyll is instrumental to glucose production and storage, albinism prevents a plant from providing food for itself; therefore, survival of albino growth is depended upon parasitic-type growth on the non-albino portions of the redwood. Albino redwoods in the wild are typically found in two forms: aerial and basal. Aerial albinos consist of a mutated branch were the foliage grows white or yellow. Basal albinos consist of entirely white or cream colored basal sprouts growing off an otherwise healthy green redwood. A chimeric redwood is a single plant organism with two or more different genotypes originating from the same bud or meristem. The normal green genotype acts as a surrogate to support the growth and survival of the albino mutation. It is not a symbiotic relationship between two separate plants. Further, due to this dependency and lack of chlorophyll, pure albino redwoods are unable to be reproduced vegetatively.

White color variation is subject to environmental conditions, particularly light exposure. For example, when grown in direct sunlight conditions, albino redwoods may turn ivory, cream, or light yellow in color. In contrast, when growing under the canopy of surrounding tree branches, albino redwoods are white in color. Excessive heat and low humidity may also result in die-back of the albino portions of the redwood. Additionally, the variation and distribution of white coloration is influenced by the phenotypic expression of three different types of chimeric growth: periclinal, sectorial, and mericlinal.

Chimerism in plants is typically achieved artificially through grafting and controlled gamma ray irradiation of seeds. One example of a grafted chimera plant is the thornless rose. A second example of irradiated seeds producing chimeric growth is the African violet plant. The present invention, in contrast, is a naturally-occurring chimeric mutation observed through variegated apical stems.

DEFINITIONS

In order to provide a clear and consistent understanding of the specification, the following definitions are provided:

A Zone. "A Zone" refers to a primary branch originating from a terminal bud. Coloration in the A Zone is predominantly green, but can range from range from albino, chimera, and non-chimeric variegation.

Albino. "Albino" refers to a white color variation ranging from ivory white to pale, yellow-green white, and is a result of a genetic mutation inhibiting chlorophyll production.

B Zone. "B Zone" refers to secondary branches developing from axillary and accessory buds from present or empty leaf axils with no primary branch present. They are commonly found between the internode of two primary branches. Coloration in the B Zone can range from albino, chimera, non-chimeric variegation, and less frequently green.

C Zone. "C Zone" refers to secondary branches developing from axillary and accessory buds in the region of the primary branch's axil or branch collar. Coloration in the C Zone can range from range from albino, chimera, non-chimeric variegation, and green.

Chimera. "Chimera" refers to the existence of more than one genotype present in one plant originating from the same bud or meristem. The chimeric phenotype is separated into three different categories based on the location and relative proportion of mutated to non-mutated cells in the apical meristem. These categories are mericlinal, periclinal, and sectorial.

Chimeric variegation. "Chimeric variegation" refers to a pronounced delineation of color with both green and white pigment in the meristems, branches, and needles.

Mericlinal chimera. "Mericlinal chimera" refers to a phenotypic expression in which only a small portion of the plant structure (stems, branches, and leaves) demonstrates chimeric albinism. This type of chimera is known in the industry to be unstable.

Non-chimeric variegation. "Non-chimeric variegation" refers to a partial lack of chlorophyll (and therefore green pigment) in plant cells and tissues where it is normally expected to be present. The pattern of variegation is unorganized and is differentiated at the cellular level between green and white. The variegation expression is mosaic in appearance.

Periclinal chimerism. "Periclinal chimerism" refers to a stable chimeric variegated mutation expressing albinism across the meristem dome. This leads to subsequent cell division of mutated and non-mutated cells within the meristem giving rise to a stable continuation of growth for both genotypes.

Primary. "Primary" as used in this application refers to branches and buds forming initially from the meristem with no rest period. Primary branches and buds develop within the "A Zone".

Secondary. "Secondary" as used in this application refers to branches and buds forming after a rest period and are latent in nature. They develop from axillary and accessory buds after Primary branch development. Secondary branches and buds are found both in "B and C Zones".

Sectorial chimera. "Sectorial chimera" refers to growth where mutated cells affect large sections of the apical meristem. Mutated tissue can extend through all cell layers within the meristematic tissue. The delineation line between both genotypes is usually vertical in arrangement through the meristem and between stomata bands in the leaves. This type of chimerism is known in the industry to be unstable.

BRIEF SUMMARY OF THE INVENTION

The following traits represent the characteristics of the new redwood tree variety 'Grand Mosaic'. These traits in combination distinguish this variety from all other commercial varieties known to the inventors.

1. A non-grafted, periclinal chimera exhibiting stable albino growth from inside the apical meristem dome;
2. Terminal buds exhibiting phenotypic color expressions of green, albino, chimera or non-chimeric variegation with varying hues within these color expressions.
3. Latent, axillary and/or accessory buds forming between the internode of primary branches, branch axils, and within the branch collar zone. These buds exhibit phenotypic color expressions of green, albino, chimera or non-chimeric variegation with varying hues within these color expressions. Frequently, axillary and/or accessory buds form in the absence of an existing branch, whether it's primary or secondary in nature.
4. Branches with habit of horizontal to drooping-like habit.
5. Moderate-to-fast growth depending on the amount of albinism compared to other common green redwoods.

The initial cross taking place in 1976 under the direction of the second-named inventor, combined the premature cones on the green redwood (Parent Two) with pollen collected from the albino redwood (Parent One). The conelets were then sealed with a plastic bag to prevent open pollination. Redwood seeds take a year to mature, so in late 1977, of the thousands of seeds present, 360 were randomly selected from the ripe cones. Within a couple of weeks, several tiny stems and cotyledons emerged displaying differences in coloration. The present invention is derived from one of the 161 surviving seedlings of this experiment. Further background on the original cross are detailed in the book entitled *The White Redwoods: Ghosts of the Forest* (Davis, D. & Holderman, D. 1980, *Naturegraph Publishers*. California. Pages 33-36).

At the time of application filing, the invention demonstrates a moderate-to-fast tree-like growth habit. It is approximately 2.48 m tall with a flat top and a stem nearly 3.12 cm in diameter. The limb spread is about 1.5 m in diameter. Sections exhibiting periclinal chimera and green foliage appear more dense then it's sibling 'Mosaic Delight' (U.S. Plant Pat. No. 26,573, hereinafter 'Mosaic Delight'). Forty-five percent of the present invention's branches exhibit periclinal chimeric growth with albino axillary bud growth. Propagated cuttings from the present invention already exhibit a faster growth rate than 'Mosaic Delight'. A determination of growth rate for the cuttings is correlated with albinism. For example, when trees exhibit ratio of 0 to 25% albino foliage to green, they exhibit moderate to fast growth. With a ratio of 25 to 60% albino foliage to green, trees have a more moderate to slow growth rate. This expression reflects the impact of lower glucose levels in trees with high albinism and the effect on growth rate.

Past experimental propagation of the present invention underwent several propagation efforts and experienced several challenges in producing vigorous, stable specimens. Finally, the present invention has been successfully and repeatedly propagated asexually in a controlled nursery environment through vegetative, leaf and stem cuttings under the direction of the first named inventor. The first viable propagation effort was conducted in the Spring of 2012 after the first-named inventor selected two hardwood cuttings taken from the present invention. The cuttings were transported to a greenhouse located in Volcano, Calif. The cuttings were divided into stem cuttings and dipped into a rooting solution consisting of 2500 PPM of IBA for approximately 10 seconds. Following this step, the stem and leaf cuttings were planted in gallon-sized pots and treated with a fungicide product. Between the Fall of 2012 through the Winter of 2012-2013, the cuttings were misted and given water at regular intervals. The cuttings were also provided supplemental lighting 24 hours a day. By the end of August of 2014 (third year), the cuttings demonstrated a sharp increased albino growth from axillary and/or accessory buds forming within the internode of primary green branches and within the branch collar zone of primary green branches. The second propagation effort was conducted in Winter of 2013 when the first-named inventor selected 32 hardwood cuttings off the present invention. The cuttings were transported to the same greenhouse located in Volcano, Calif. and propagated under the same environmental conditions and protocol procedures carried out in Spring 2012. By the Spring of 2016 (beginning the fourth year), the 10 surviving cuttings demonstrated increased albino growth from axillary and/or accessory buds forming within the internode of primary green branches and within the branch collar zone of green branches. Based on the results between the 2012 propagation group and the 2013 propagation group, the invention shows better rooting results with hardwood cutting propagation taken from summer growth rather than winter growth.

The cuttings of the present invention, 'Grand Mosaic', have demonstrate that the combination of characteristics disclosed are stable and firmly fixed, and are retained true-to-type through the periclinal chimera genotypes. It is important to note that the invention can exhibit mericlinal and sectorial growth through the periclinal phenotype and therefore this growth is claimed within this invention. It is known in the literature that periclinal chimerism in plants is considered stable and as such, is readily available in commercial markets (Lineberger, R. No date. Origin, Development, and Propagation of Chimeras. Texas A&M University. Retrieved from aggie-horticulture.tamu.edu/tisscult/chimeras/chimeralec/chimeras.html on Jan. 20, 2014).

During propagation experimentation, one cutting was selected for a fertilizer test and the conclusion of the test elucidates that a slow release fertilizer works best with 'Grand Mosaic' and quick release fertilizers should be avoided.

Propagation experiments reveal that coloration and growth rates will vary somewhat between cuttings depending on whether the cutting is taken from the stem or the leaf. Table 1 illustrates the variations of the two original cuttings taken from the 2012 group and four cuttings taken from the 2013 group. Data was collected in the Fall of 2014, (as documented in Line One for Cutting Number 1) Spring 2015, (as documented in Line Two for Cutting Number 1 and Line One for Cutting Number 2), early Winter of 2016, (as documented in Line Three for Cutting Number 1, Line Two for Cutting Number 2, and Line One for Cuttings Number 3 through Number 6), and Summer of 2016, (documented in Line Four for Cutting Number 1, Line Three for Cutting Number 2, and Line Two for Cuttings Number 3 through Number 6).

TABLE 1

COLORATION AND GROWTH RATE COMPARISON

| Cutting | Type of Cutting | Height (cm) | New vertical growth (cm) | Growth (duration in (months | Axillary bud albinism (%) |
|---|---|---|---|---|---|
| #1 | stem | 25.4 | 136.6 | 12-40 | 5% |
| #1 | stem | 205 | 43 | 40-47 | 30% |
| #1 | stem | 209 | 4 | 47-55 | 45% |
| #1 | stem | 248.9 | 39.9 | 55-63 | 45% |
| #2 | stem | 20.3 | 38.1 | 12-49 | 5% |
| #2 | stem | 97.8 | 39.4 | 49-55 | 20% |
| #2 | stem | 143.5 | 45.7 | 55-63 | 22% |
| #3 | stem | 20.3 | 83.2 | 12-43 | 10% |
| #3 | stem | 144.8 | 41.2 | 43-51 | 20% |
| #4 | leaf | 33.0 | 73.7 | 12-43 | 1% |
| #4 | leaf | 182.9 | 76.2 | 43-51 | 1% |
| #5 | leaf | 31.7 | 80.0 | 12-43 | 0% |
| #5 | leaf | 143.5 | 31.8 | 43-51 | 1% |
| #6 | stem | 17.7 | 43.2 | 12-43 | 10% |
| #6 | stem | 97.8 | 36.9 | 43-51 | 20% |

| Cutting | Tree canopy with terminal or lateral bud albinism (%) | Number of variegated secondary buds | Cutting pro-pagated (year) | Age measured (months) |
|---|---|---|---|---|
| #1 | 0% | 12 | 2012 | 40 months |
| #1 | 2% | No Data | 2012 | 47 months |
| #1 | 5% | 31 | 2012 | 55 months |
| #1 | 5% | 93 | 2012 | 63 months |
| #2 | 0% | No Data | 2012 | 47 months |
| #2 | 0% | No Data | 2012 | 55 months |
| #2 | 6% | 22 | 2012 | 63 months |
| #3 | 0% | No Data | 2013 | 31 months |
| #3 | 9% | 11 | 2013 | 39 months |
| #4 | 0% | No Data | 2013 | 31 months |
| #4 | 0% | 3 | 2013 | 39 months |
| #5 | 1% | No Data | 2013 | 31 months |
| #5 | 2% | 1 | 2013 | 39 months |
| #6 | 0% | No Data | 2013 | 31 months |
| #6 | 10% | 5 | 2013 | 39 months |

It is known in the literature that conifers (redwoods) may experience delayed axillary bud emergence from the meristem (for example, see Fink, S. 1984. Some Cases of Delayed or Induced Development of Axillary Buds From Persisting Detached Meristems in Conifers. *Amer. J. Bot.* 71(1) Pages 44-51). This natural delay has been observed in the present invention, wherein latent white terminal, axillary, and accessory buds emerged from established green branches at least 2 to 4 years after the initial meristem growth even though the cuttings were grown under the same conditions. For example, between the age of forty and forty-seven months, Cutting Number 1 increased its albinism from 5 percent to 30 percent, Cutting Number 2, between forty-seven and fifty five months, accelerated its primary green growth and increased its albinism from 5 percent to 20 percent. Another example is Cutting Number 5 from the 2013 group, which didn't start showing variegation until the 39$^{th}$ month. The delayed development of the albino genotype within 'Grand Mosaic' allows better establishment and stronger primary growth from the green genotype. The delayed albinism emergence suggests why the invention holds a better tree form than sibling 'Mosaic Delight'. It is important to note the very low percentage of primary buds originating from (A zone) producing "visible" chimeric albinism. This demonstrates traits of genotypic stability where the invention favors a "primary" green growth habit in contrast to a "secondary" chimeric growth habit. This arrangement lends itself to the green genotype predominately developing a strong green leader which further promotes vertical growth within the invention. Based on the observed data, stem cuttings become better established and display variegation earlier than leaf cuttings. Note: the data reflects only 4.0 cm of vertical growth between the 47$^{th}$ and 55$^{th}$ month due to the removal of 30.5 cm of the apical meristem for propagation purposes.

Plant Breeder's Rights for this variety have not been applied for and 'Grand Mosaic' has not been offered for sale more than a year before the filing date of this application, nor has it been offered for sale under another variety name. Since the original cross, cuttings of 'Grand Mosaic' have undergone experimental use to solve prior propagation challenges and the present invention has not been publicly available during this time.

Plants of the present invention have not been observed under all possible environmental and cultural conditions. The phenotype may vary somewhat with variations in environmental conditions without, however, any variance in genotypes. For example, phenotypic expression may vary somewhat with fluctuations in temperature, light intensity and soil chemistry.

BRIEF DESCRIPTION OF THE PHOTOGRAPHS

The accompanying colored photographs illustrate the overall appearance of the new and distinct albino redwood tree with periclinal chimerism showing the colors as true as it is reasonably possible to obtain in colored reproductions of conventional photography. The photographs were taken in a greenhouse setting under defused, natural lighting. Two typical specimens (Stem Cutting Numbers 1 and 2) of the present invention are included to demonstrate color variation on the leaves and stems produced by the chimeric and non-chimeric genotypes.

FIG. 1 (taken Oct. 20, 2014 of Stem Cutting Number 1 at 40 months-old) demonstrates approximately 5% variegation. This illustrates the latency of the chimeric albino growth characteristic of 'Grand Mosaic' in the first few years of growth. Its typical with this new variety to have a majority of the green genotype emerge first in primary growth.

Figure 2:
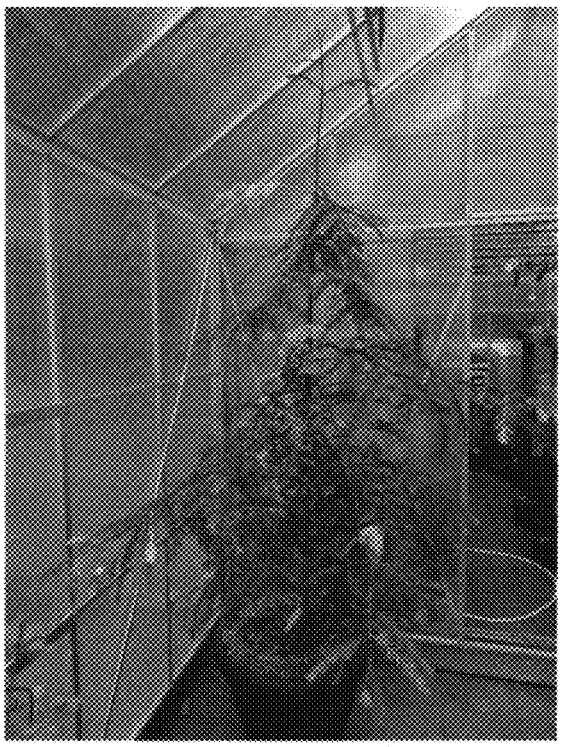

FIG. 2 (taken May 13, 2015 of Stem Cutting Number 1 at 47 months-old) demonstrates a marked increase of chimeric albino growth. At this stage of growth, the invention exhibits approximately 30% chimeric albino foliage. One of the distinguishing characteristics of the invention's is seen in its apical dominance. This photograph also demonstrates the invention's horizontal to drooping-like growth habit.

Figure 3:
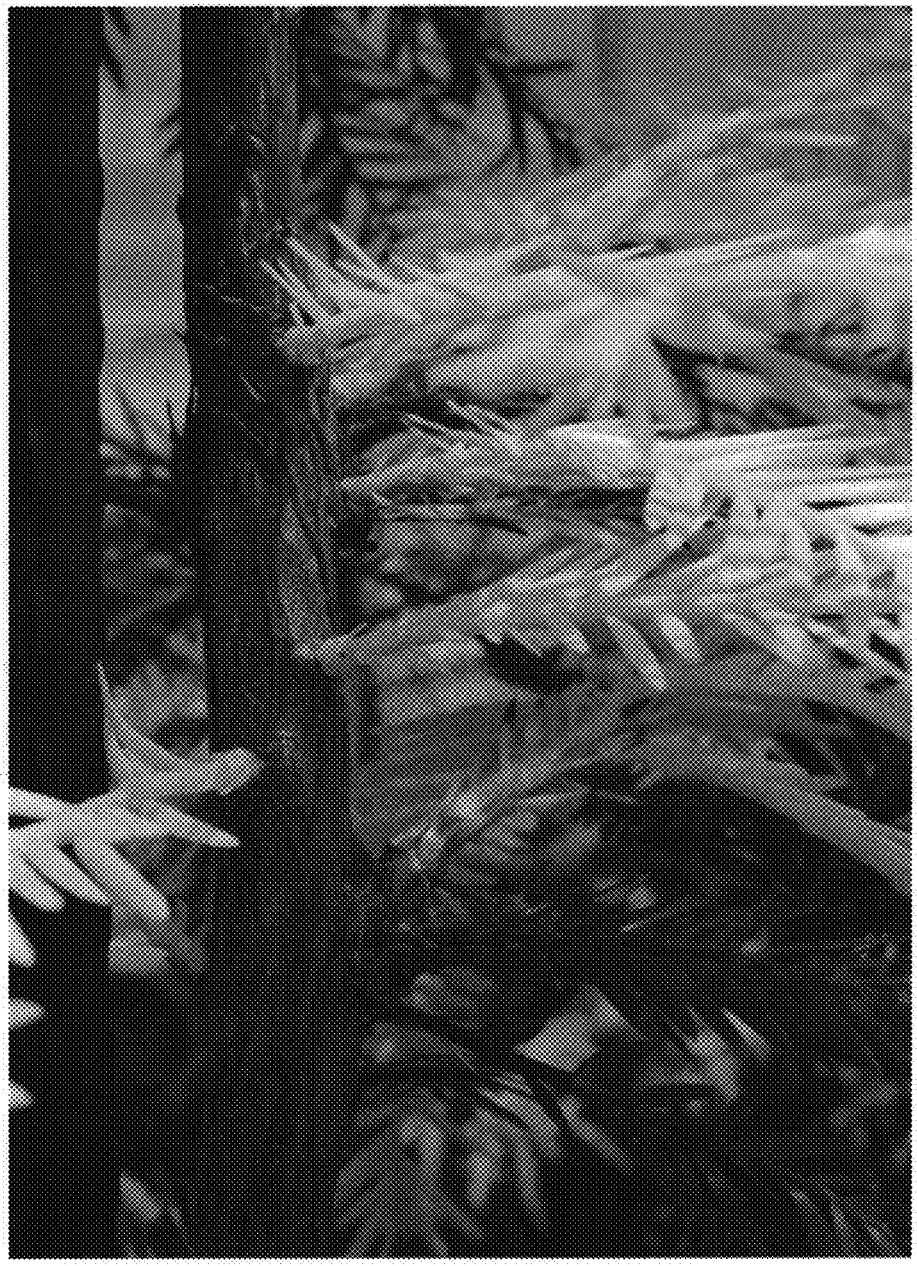

FIG. 3 (taken May 26, 2015 of Stem Cutting Number 1 at 47 months-old) is a close-up image demonstrating the periclinal chimeric albinism originating from the apical meristem dome and displaying axillary and/or accessory buds forming within the internode of established green branches. These buds form in empty leaf axils along the main stem between the internode of established primary green branches of the invention. There are also axillary and/or accessory buds exhibiting periclinal chimeric albinism in and around the branch collar zones of primary and secondary branches exhibiting green and white variegation.

Figure 3A:
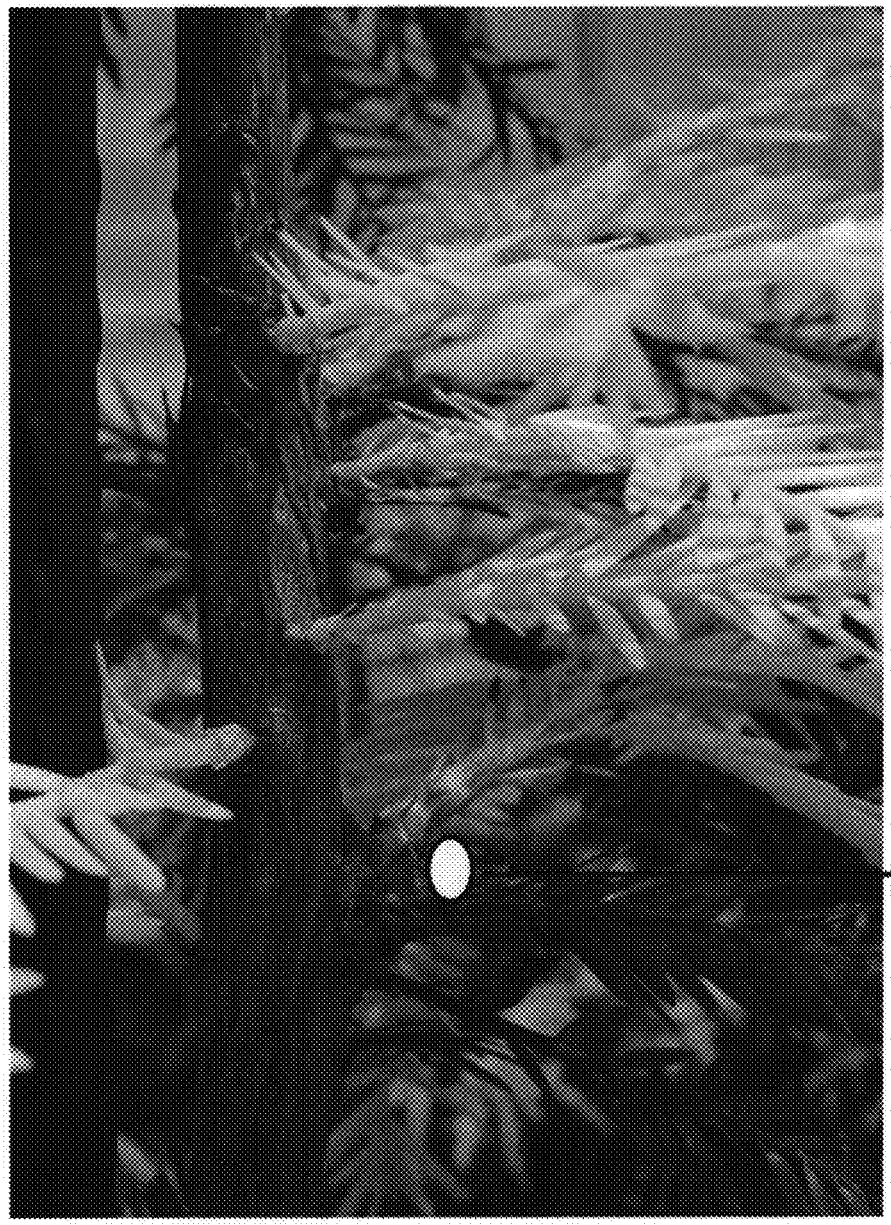

FIG. 3*a* (taken May 26, 2015 of Stem Cutting Number 1 at 47 months-old) is similar to FIG. 3 except that Zones A are labeled with the number 1 to demonstrate the arrangement of the primary and secondary branches of all zones.

Figure 3B:
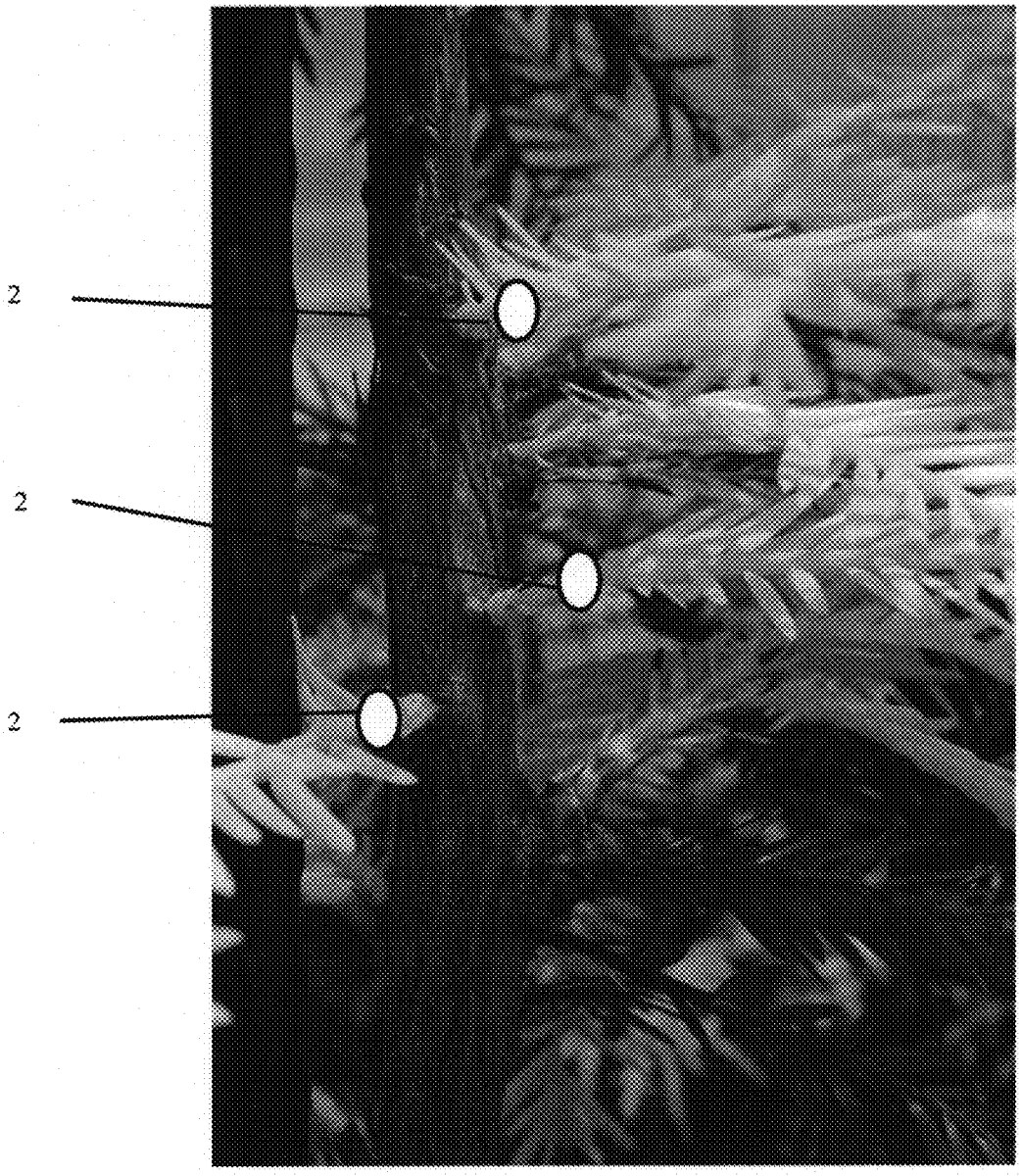

FIG. 3*b* (taken May 26, 2015 of Stem Cutting Number 1 at 47 months-old) is similar to FIG. 3 except that Zones B are labeled with the number 2 to demonstrate the arrangement of the primary and secondary branches of all zones.

Figure 3C:
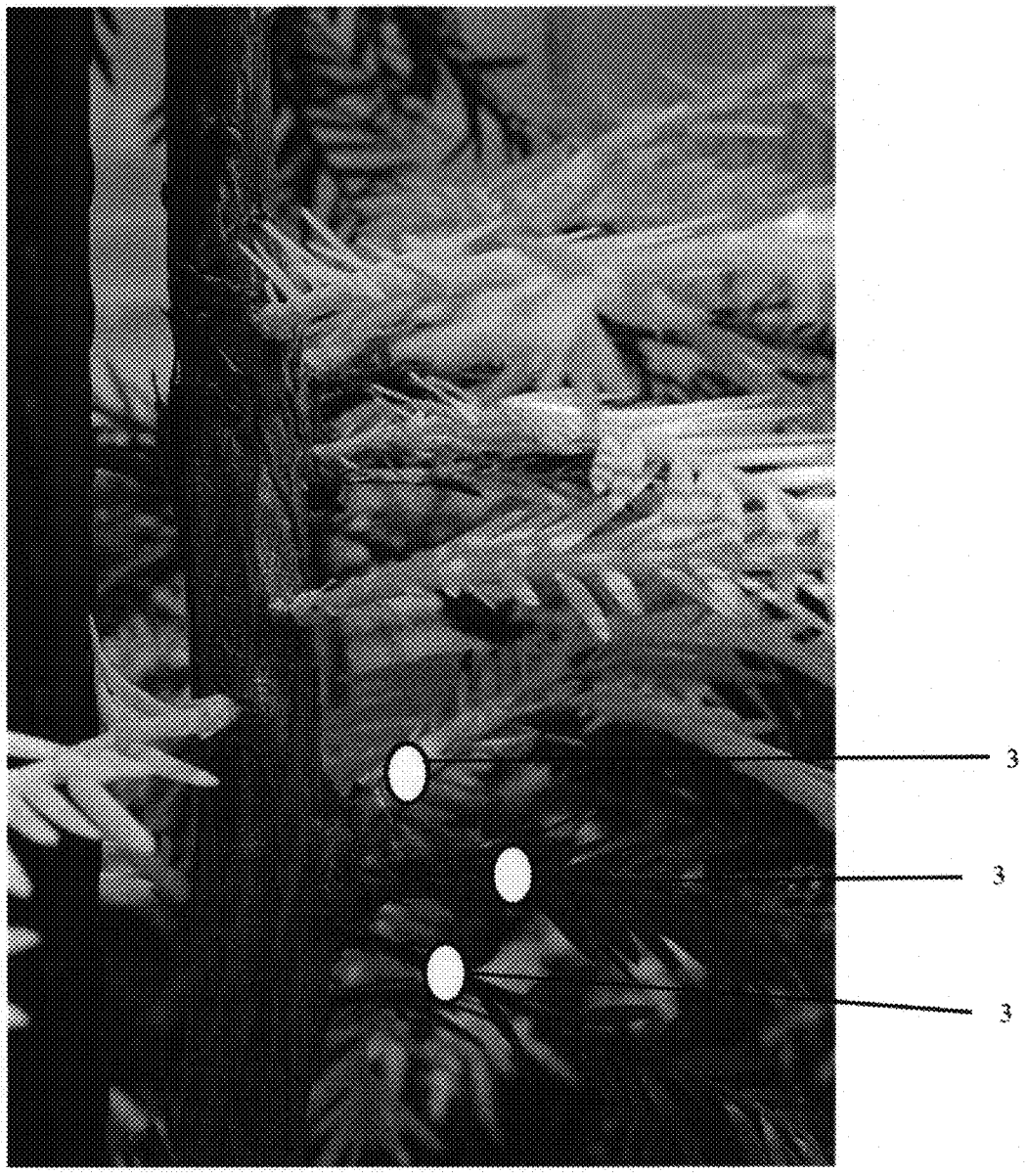

FIG. 3*c* (taken May 26, 2015 of Stem Cutting Number 1 at 47 months-old) is similar to FIG. 3 except that Zones C are labeled with the number 3 to demonstrate the arrangement of the primary and secondary branches of all zones.

Figure 4:
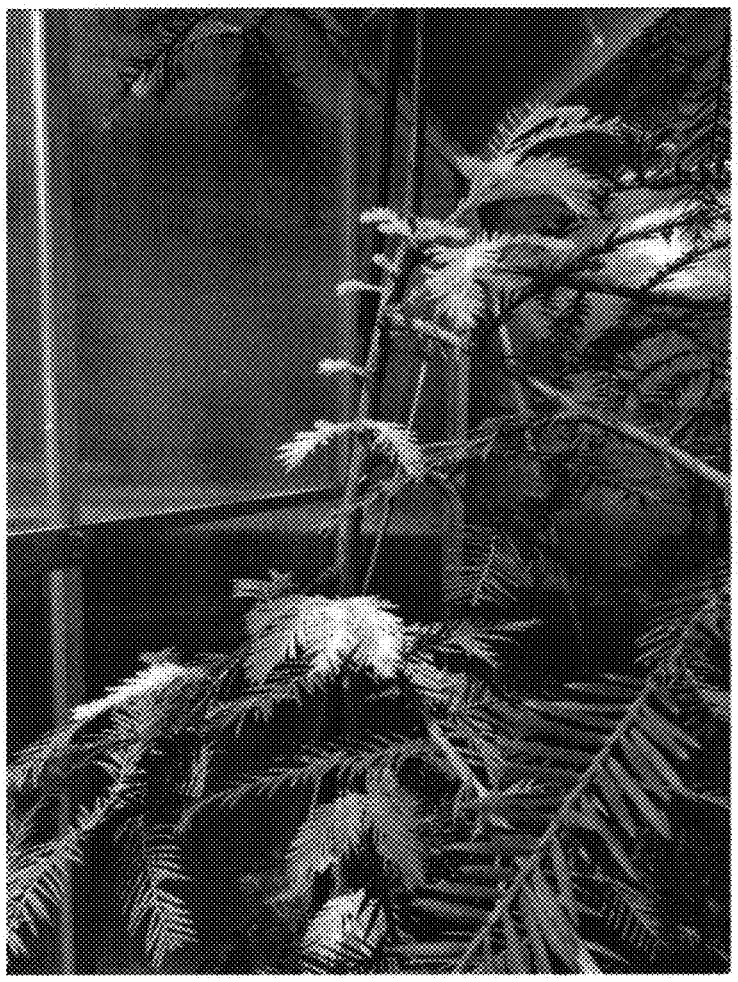

FIG. 4 (taken Apr. 15, 2015 of Stem Cutting Number 1 at 46 months-old) demonstrates chimeric albino expression on secondary branches arising from an internode's B Zone.

Figure 5:
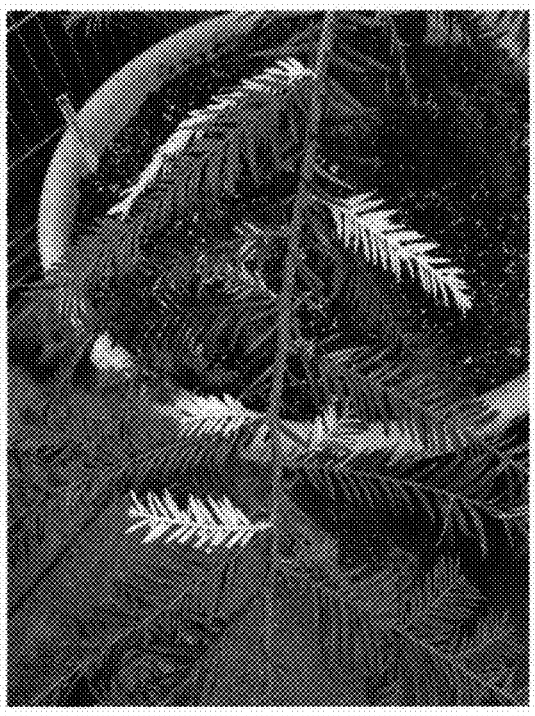

FIG. 5 (taken Oct. 17, 2015 of Stem Cutting Number 2 at 52 months-old) demonstrates chimeric albino expression on secondary branches arising from the branch collar's C Zone.

Figure 6:
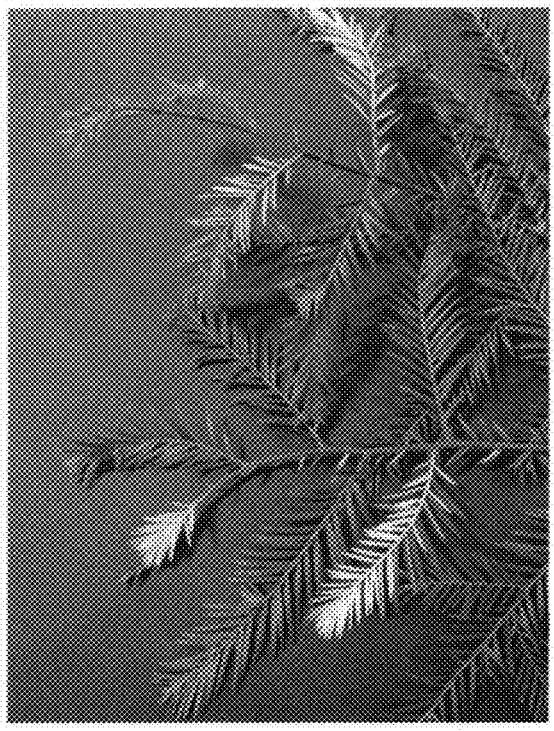

FIG. 6 (taken May 15, 2015 of Stem Cutting Number 1 at 47 months-old) demonstrates a three-month-old branch exhibiting periclinal chimeric albinism originating from new lateral buds. Note the absence of chimeric axillary or accessory bud growth at this stage.

Figure 7:
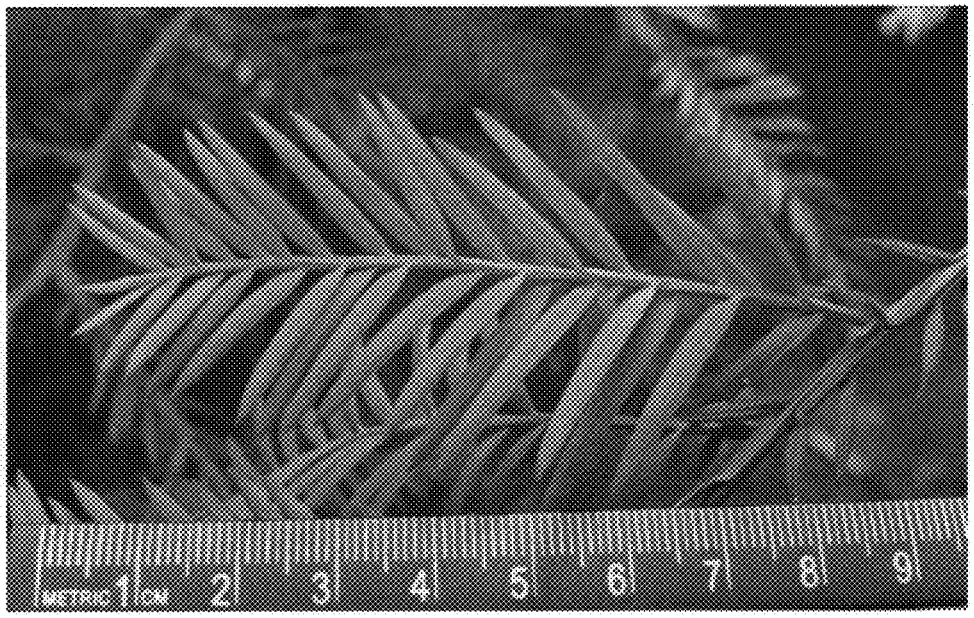

FIG. 7 (taken Jan. 11, 2015 of Stem Cutting Number 1 at 43 months-old) demonstrates the broad needles and light green coloration.

Figure 8:
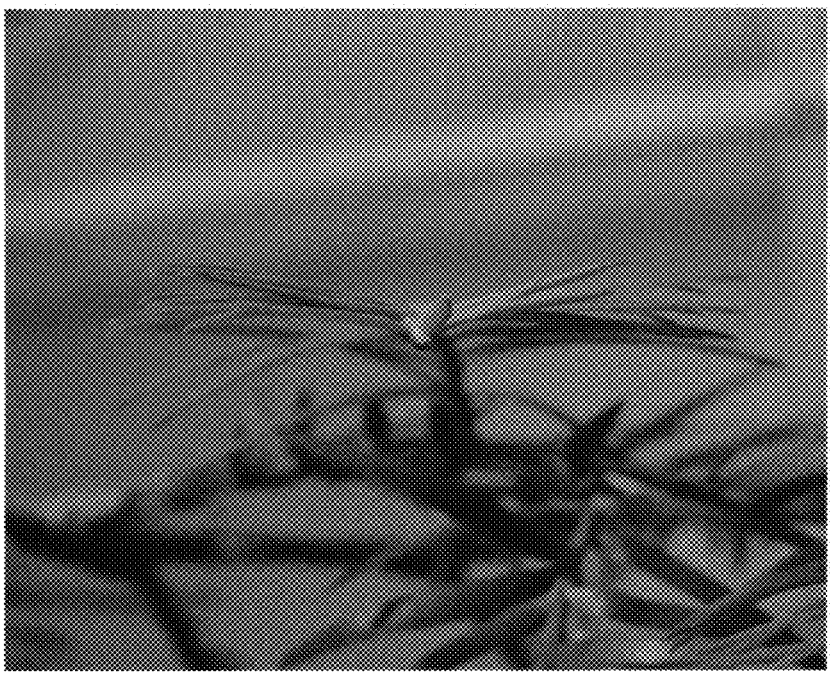

FIG. 8 (taken Jan. 11, 2015 of Stem Cutting Number 1 at 43 months-old) shown with direct view of the branchlet, exhibits a large horizontal needle pattern.

Figure 9:
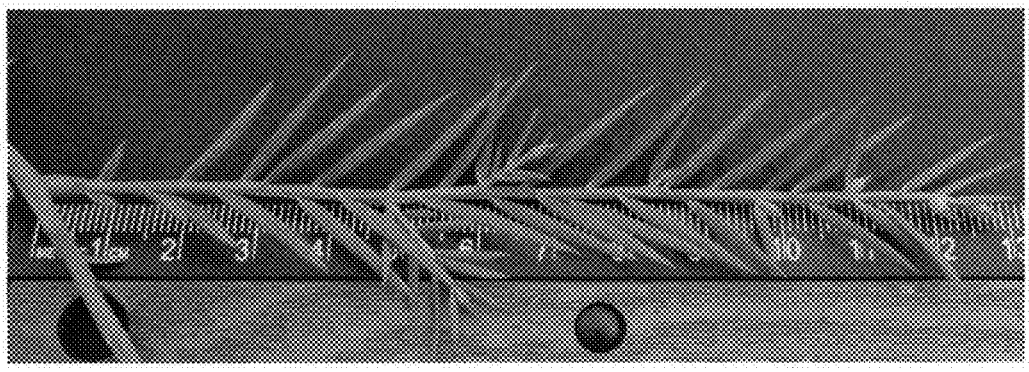

FIG. 9 (taken Jan. 11, 2015 of sibling 'Mosaic Delight'), presented as a comparison variety, demonstrates an open needle arrangement on the branchlets. Needles exhibit a more narrow and wiry appearance compared to the present invention.

Figure 10:
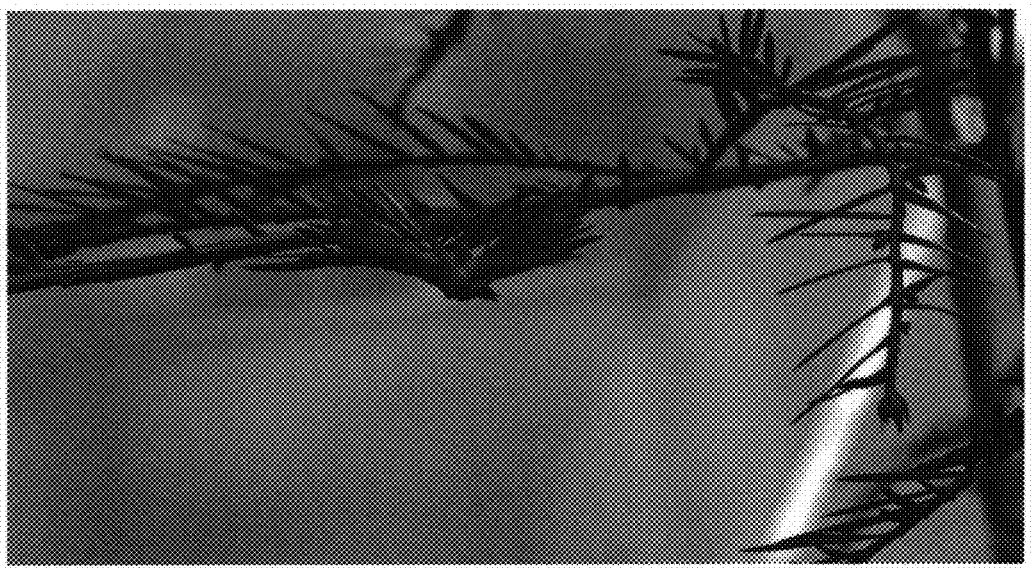

FIG. 10 (taken Jan. 11, 2015 of sibling 'Mosaic Delight'), presented as a comparison variety, demonstrates the upturned "V" needle pattern seen on a direct view of the branchlet.

Figure 11:
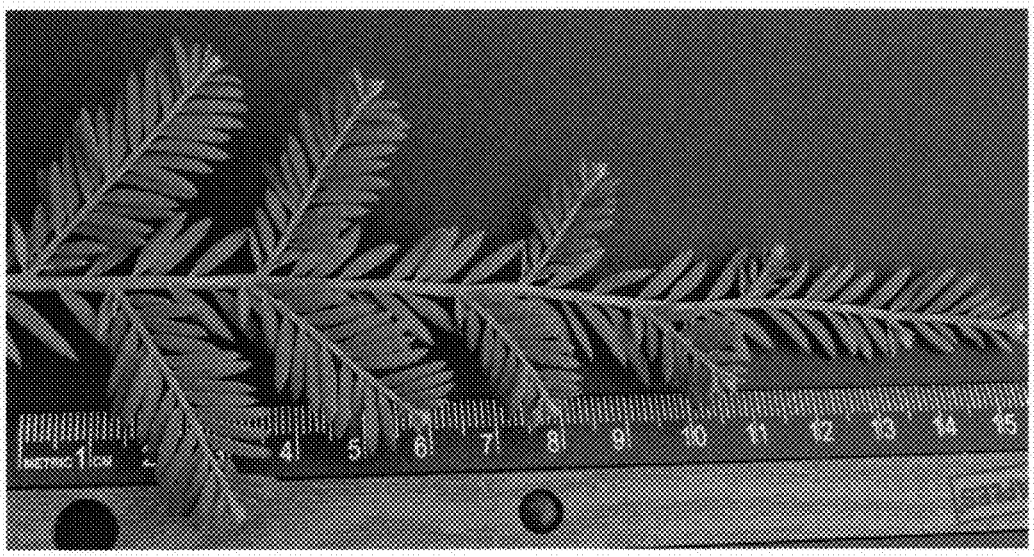

FIG. 11 (taken Jan. 11, 2015 of sibling 'Early Snow' (U.S. patent application Ser. No. 15/530,139; hereinafter 'Early Snow')), presented as a comparison variety, exhibits sub-branchlets that taper to a point on primary branches. Needles on this variety tend to overlap on the branchlet leaving fewer gaps between needles compared to siblings 'Mosaic Delight' and the present invention.

Figure 12:
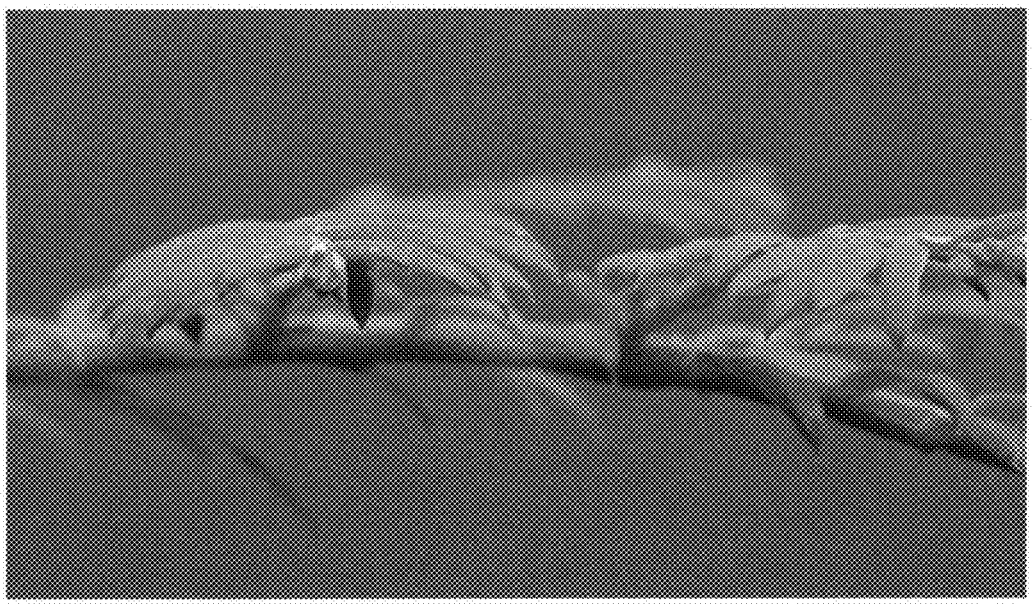

FIG. 12 (taken Jan. 11, 2015 of sibling 'Early Snow'), presented as a comparison variety, is shown with a direct view of the branchlet exhibiting a concave down needle pattern.

Figure 13:
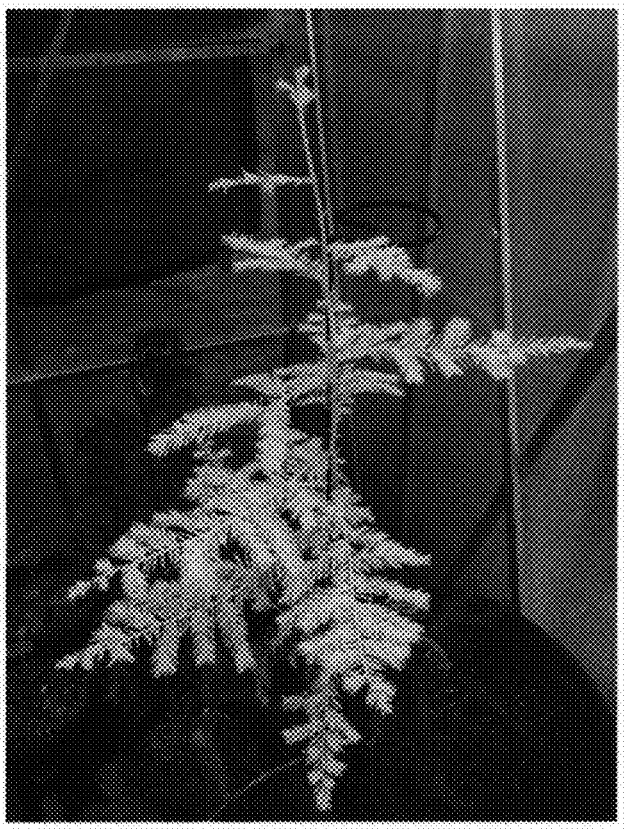

FIG. 13 (taken in taken in 2014), presented as a comparison variety, is of a redwood with chimeric albinism bred by the first named inventor. This variety named 'Christmas Tree' exhibits predominantly white coloration on primary branches while the secondary branches are expressed mostly in the normal green genotype.

DETAILED BOTANICAL DESCRIPTION

The following is a detailed botanical description of the new variety 'Grand Mosaic'. Data was collected from Stem Cutting Number 1 at 52 months-old in the Fall of 2015; presently growing in a greenhouse in Volcano, Calif. The growing conditions approximate those generally used in commercial practice. Color readings were observed indoors with natural lighting diffused through greenhouse panes. The color determinations are in accordance with the Fifth Edition (2007) of The Royal Horticultural Society Colour Chart published by The Royal Horticultural Society (London, England), except where general color terms of ordinary dictionary significance are used. Chimeric and non-chimeric expression among the propagated trees leads to a variation in color and, therefore, a color's hue, saturation, or intensity is generally depicted in The R.H.S. colour charts through the follow color groups and ranges: RHS 4C-D, 8D (yellow group), 128A-149D (green group), and 155A-D, NN155-159D, 157A-158D, 189A-196D (grey group). The below listed color ranges, while not observed at the time of recording the characteristics, are included to provide potential color variations due to variable growing conditions, including but not limited to: weathering and moisture exposure. Variegated color descriptions include both chimeric and non-chimeric expression.

VARIETY DESCRIPTION

Classification:

*Family*.—Cupressaceae.

*Botanical*.—*Sequoia sempervirens*.

*Common*.—Coast Redwood tree.

Parentage:

*Parent one*.—Unnamed Albino *Sequoia sempervirens* (neither patented, nor commercially available).

*Parent two*.—Unconfirmed variety of Green *Sequoia sempervirens* (however, it is most likely that Parent Two is neither patented, nor commercially available).

Propagation: Vegetative via leaf and stem cuttings.

Plant:

*Ploidy*.—Hexaploid.

*Height, unpruned* (*m*).—209.4 cm (measured at 48 months); potential mature height of 18 to 40 m.

*Vigor*.—Strong.

*Shape*.—Pyramidal.

*Growth rate*.—Moderate-to-fast depending on albinism present.

*Growth habit*.—Horizontal to pendulous.

*Canopy width* (*m*).—168.3 cm.

*Canopy height* (*m*).—209.4 cm.

*Crown shape*.—Pyramidal.

Trunk and branchlets:

*Trunk texture*.—Smooth as cuttings, emerging to fibrous at approximately four years.

*Trunk diameter* (*cm*).—2.0 cm taken at 2.0 cm above the ground.

*Bark color* (*of a* 2 *to* 3-*year-old tree*).—RHS 165A and 200D; with a range of 164A-N167D, 173A-178D, and 200A-D.

*Branchlet length* (*m*).—97.2 cm measured from stem.

*Branchlet diameter, average* (*mm*).—5.0 mm.

*Branchlet texture*.—Smooth and waxy.

*Branchlet color*.—Variation due to chimeric expression, including: green, white, chimeric, or non-chimeric variegated. New growth, green branchlet: RHS 144A and C (green group), with a range of 138A-139D, and 143A-D (green group). Old growth, green branchlet: RHS 137B, (green group), with a range of RHS 137A-N137D (green group). New growth, albino branchlet: RHS 4D and 8D, (yellow group) with a range of 4C and 8C (yellow group), and a range of 158C-D (grey group). Old growth albino branchlet: RHS 4D and 8D, (yellow group), with a range of 4C and 8C (yellow group), and a range of 158C-D (grey group). Variegated branchlet: Ranging from RHS 4D and 8D (yellow group) to RHS 128A-149D (green group) to RHS 155A-D, NN155-159D, 157A-158D, and 189A-196D (grey group).

*Branchlet arrangement*.—Alternate.

*Crotch angle from main trunk*.—Green branches: Horizontal range from 30° to 0° and dropping range from 360° to 300°. Albino, chimeric, or non-chimeric variegated branches: Approximately 315° to 40°.

*Meristematic bud*.—a. Shape: Scaly. b. Color: Apical meristem: Chimeric. Lateral buds, axillary and/or accessory buds forming in and around the branch collar zone exhibiting phenotypic color expressions ranging from green, albino, chimera or non-chimeric variegation. Green bud: RHS 144A, with a range of RHS 138A-139D, 143A-D, and 144A-C (green group). White bud: RHS 4D and 8D (yellow group), with a range of RHS 4C and 8C (yellow group), and 158C-D (grey group). Variegated bud: Range of RHS 4C-D to 8D (yellow group) and a range of RHS 128A-149D (green group) and a range of 155A-D, NN155-159D, 157A-158D, and 189A-196D (grey group). c. Bud-union characteristics: Axillary.

Burl: None observed.

Scion:

*Circumference* (*leaf cuttings*).—3.5 cm.

*Height at which measurement taken*.—17.8 cm at time of planting and 248.9 cm for stem cuttings.

*Suckering*.—None observed.

Leaves:

*Arrangement*.—Flat needles in alternating patterns.

*Texture*.—Glabrous (smooth).

*Type*.—Simple.

*Shape*.—Needle-like. Needle tip shape: Acute or acuminate.

*Cross section*.—Concave 1.0 mm.

*Leaf needle length* (*mm*).—1.0 to 3.5 cm.

*Leaf needle width* (*mm*).—0.5 to 1.0 cm.

*Surface*.—a. Upper surface texture: Glabrous (smooth, waxy). b. Surface color (upper and lower): Green, white, chimeric, or non-chimeric variegated-specifically: New growth, green needle (upper surface): RHS 144A and C (green group), with a range of 138A-139D and 143A-D (green group). New growth, green needle (lower surface): RHS 143C (green group), with a range of 138A-139-D, 143A-D (green group), and range of 191A-B (grey group). Old growth, green needle (upper surface): RHS N137B (green group), with a range of 137A-N137D (green group). Old growth, green needle (lower surface): RHS 191A (grey group), with a range of 138A-139D (green group) and range of 191A-C (grey group). New growth, albino needle (upper surface): RHS 4D and 8D (yellow group), with a range of 4C and 8C (yellow group), and range of 158C-D (grey group). New growth, albino needle (lower surface): RHS 4D and 8D (yellow group), with a range of 4C and 8C (yellow group), and range of 158C-D (grey group). Old growth, albino needle (upper surface): RHS 4D and 8D (yellow group), with a range of 4C and 8C (yellow group), and range of 158C-D (grey group). Old growth, albino needle (lower surface): RHS 4D and 8D (yellow group), with a range of 4C and 8C (yellow group) and range of 158C-D (grey group). Variegated needles in all locations: RHS 4C-D and 8D (yellow group), RHS 128A-149D (green group), and RHS 155A-D, NN155-159D, 157A-158D, and 189A-196D (grey group). c. Stomata band(s) on lower needle: Present, 2 bands.

*Petiole*.—a. Shape: Oval and scale-like. b. Color: Green, white, chimeric, or non-chimeric variegated, specifically: New growth, green petiole: RHS 144 A and C (green group), with a range of 138A-139D, and143A-D (green group). Old growth, green petiole: RHS 137B (green group) with a range of 137A-N137D (green group). New growth, albino petiole: RHS 4D and 8D (yellow group), with a range of 4C and 8C (yellow group), and range of 158C-D (grey group). Old growth, albino petiole: RHS 4D and 8D (yellow group), with a range of 4C and 8C (yellow group), and range of 158C-D (grey group). Variegated petiole: A range between RHS 4C-D and 8D (yellow group) and RHS 128-149 (green group) and a range of 155A-D, NN155-159D, 157A-158D, and 189A-196D (grey group). c. Thorns (spines): Absent. d. Length (average): 0.5 mm to 1.0 mm (leaf lamina narrows down proximally).

Cones: None observed.

Flowers: None observed.

Reproductive organs: None observed.

Best mode growing conditions:

*Soil conditions*.—Deep, well-drained loam and clay-loam soil.

*Water use/drought tolerance*.—Require regular watering when young; however, once established, trees are mildly drought tolerant with optimal growing conditions including an annual rainfall exceeding 102 cm per year.

*Temperature*.—Best grown in cool climates ranging from 50° F. to 80° F. with frost-free winters.

*Fertilization*.—a. Propagation: Potting soil with slow release fertilizer.

*Maintenance*.—Slow release fertilizer.

Resistance to disease: Low susceptibility to disease due to tannin content; however, may be subject to *Botryosphaeria* sp. canker if under stress conditions (for example, drought).

COMPARISON TO SIMILAR VARIETIES

Parent One is a non-chimeric variegated albino *Sequoia sempervirens* demonstrating ninety-five percent albinism with approximately five percent non-chimeric variegation on the new growth and a hedge-bush-like growth habit. Unlike Parent One, 'Grand Mosaic' displays both chimeric and non-chimeric variegated growth. Specifically, 'Grand Mosaic' demonstrates stable green and chimeric albino growth from inside the apical meristem with albino to mosaic variegation displayed on terminal, lateral, adventitious, axillary, and accessory buds. These buds form between the internode of established green branches, inside present or empty branch axils and within the branch collar zone. 'Grand Mosaic' also demonstrates horizontal to weeping-like chimeric branches that are either green, albino, or chimeric (periclinal, mericlinal, or sectorial).

The exact parentage of Parent Two is unconfirmed; however, during the 1976 cross, Parent One was crossed with several nearby standard green *Sequoia sempervirens* exhibiting characters typical of redwoods grown locally in Santa Cruz, Calif. Unfortunately, precise records of the crosses do not elucidate which of the potential green *Sequoia sempervirens* is the female parent of this invention. Typical of the trees in this location, Parent Two is an old growth, and slow-growing tree without any variegation or chimeric albino growth. In contrast, 'Grand Mosaic' grows at a moderate-to-fast rate, and displays a range of coloration through the chimeric and non-chimeric variegated growth.

The commercially available *Sequoia sempervirens* named 'Aptos blue' (unpatented) demonstrates blue-green foliage and an upright habit with small weeping side branches; whereas, 'Grand Mosaic' foliage ranges in color from green, albino, chimeric, and non-chimeric variegated, and has horizontal to drooping branches.

'Christmas Tree' (unpatented) (see FIG. 13) is a periclinal chimeric redwood tree bred under the direction of the first named inventor. The tree is neither patented nor commercially available. The albinism in this variety is expressed differently than 'Grand Mosaic' in that 'Christmas Tree' is predominantly white on primary branches while the secondary branches are expressed mostly in the normal green genotype. Also, the meristematic cells of 'Christmas Tree' exhibit mostly a white over green arrangement whereas 'Grand Mosaic' cell layers exhibit predominantly a green over white arrangement in the meristem.

Sibling variety 'Early Snow' (U.S. Plant Pat. No. 29,217) exhibits similar chimeric albino expressions to 'Grand Mosaic' with notable differences. Axillary and accessory buds forming in the 'B' zone (between primary branches) on 'Grand Mosaic' predominately form from empty leaf axil where with 'Early Snow' a needle is usually present. Also, 'Grand Mosaic' exhibits strong apical dominance and long needles; whereas 'Early Snow' exhibits weak apical dominance and short to medium length needles.

Sibling variety 'Mosaic Delight' exhibits similar chimeric albino expressions to 'Grand Mosaic' with notable differences. Needles on 'Grand Mosaic' are lighter green and broader in appearance compared to 'Mosaic Delight', which has narrow and darker green coloration. 'Grand Mosaic' exhibits a 2 to 4-year delay in chimeric albino expression as compared to 'Mosaic Delight', where chimeric albinism appearance is delayed by approximately one year. 'Grand Mosaic' exhibits higher chimeric albino growth within the internode region of established green branches than in 'Mosaic Delight', which primarily expresses chimeric albino growth from the branch collar zone of established branches. 'Grand Mosaic' exhibits stronger apical dominance compared to 'Mosaic Delight' which is mostly apically weak in stature.

Table 2 further distinguishes between the invention and its siblings. One clone from each of the siblings propagated in 2012 was measured for total height. Then all "B Zone" and "C Zone" secondary branches were counted on each siblings' main axis. After the count, a ratio of B to C Zone was established to determine the percentages of each. Since each invention's height varies, the total of each B and C Zones was divided into the height of the tree to determine the average height (centimeters) for B and C Zone branches respectively. The data tabulated below illustrates the different growing patterns discovered within B and C Zone secondary branches and was collected the Spring of 2015.

TABLE 2

COMPARISON OF SECONDARY BRANCHES PATTERNS AMONG SIBLINGS

| Date Jun. 2, 2015 | Height (cm) | Age | Number B & C | Percentage B & C | B & C per cm on main axis | Secondary development after primary |
|---|---|---|---|---|---|---|
| 'Mosaic Delight' (invention sibling) | 159.4 | 4 years | B = 10 C = 35 | B = 22% C = 78% | B = 15.9 cm C = 4.6 cm | 1-2 years |
| 'Grand Mosaic' | 221.6 | 4 years | B = 27 C = 14 | B = 66% C = 34% | B = 8.2 cm C = 15.8 cm | 2-4 years |
| 'Early Snow' | 97.2 | 2 years | B = 20 C = 19 | B = 51% C = 49% | B = 4.9 cm C = 5.1 cm | 1-2 years |

Table 3 presents a side by side comparison of the sibling varieties from the original cross experiments conducted in 1976. The siblings were grown in the same environmental conditions and exhibit the following similarities and differences.

TABLE 3

COMPREHENSIVE GROWTH PATTERNS COMPARISON AMONG SIBLINGS

| Characteristic | 'Mosaic Delight' Sibling (U.S. Plant Pat. No. 26,573) | 'Grand Mosaic' Sibling (present application) | 'Early Snow' (U.S. Plant Pat. No. 29,217) |
|---|---|---|---|
| Growth rate | Weak | Strong | Strong |
| Apical dominance | Weak | Strong | Weak |
| Albino expression | 1-year delay | 2 to 4-year delay | 1 year delay |
| Albino growth in internode | Lower | Higher | Higher |
| Majority of "B" zone buds found | Leaf axils | Accessory buds and empty leaf axils | Leaf axils |
| Needle angle | "V" shaped | Horizontal | Concave down |
| Needle density | Open | Dense | Dense & overlapping |
| Needle length | Medium | Long | Short to medium |
| Needle shape: Linear | Linear with Acuminate tips | Linear with Acuminate tips | Linear with Obtuse, mucronate and acuminate tips |
| Needle color | Dark green | Light Green | Dark green |
| Branchlet shape | Narrow towards blunt end | Wide towards a blunt end | Tapers towards a blunt end |

We claim:

1. A new and distinct variety of albino chimeric redwood tree, as illustrated and described herein.

* * * * *